（12） United States Patent
Soldin

(10) Patent No.: US 7,473,560 B2
(45) Date of Patent: ***Jan. 6, 2009

(54) STEROID HORMONE ANALYSIS BY MASS SPECTROMETRY

(75) Inventor: Steven J. Soldin, Bethesda, MD (US)

(73) Assignee: Georgetown University, Washington, DC (US)

( * ) Notice: Subject to any disclaimer, the term of this patent is extended or adjusted under 35 U.S.C. 154(b) by 623 days.

This patent is subject to a terminal disclaimer.

(21) Appl. No.: 10/823,691

(22) Filed: Apr. 14, 2004

(65) Prior Publication Data

US 2004/0235193 A1 Nov. 25, 2004

Related U.S. Application Data

(60) Provisional application No. 60/462,746, filed on Apr. 14, 2003.

(51) Int. Cl.
*G01N 24/00* (2006.01)
*G01N 33/92* (2006.01)

(52) U.S. Cl. .......................... 436/173; 436/63; 436/71; 436/161; 436/174; 436/175; 436/177; 436/127; 422/68.1; 250/281; 250/282

(58) Field of Classification Search .................. 436/63, 436/71, 161, 173, 174, 175, 177, 178, 127, 436/518; 422/68.1, 70; 250/281, 282
See application file for complete search history.

(56) References Cited

U.S. PATENT DOCUMENTS

| 3,997,298 | A | | 12/1976 | McLafferty et al. | |
|---|---|---|---|---|---|
| 6,541,263 | B2 | * | 4/2003 | Gao | 436/71 |
| 6,800,489 | B2 | * | 10/2004 | Dooley | 436/173 |

FOREIGN PATENT DOCUMENTS

WO    WO 01/88548    11/2001

OTHER PUBLICATIONS

Kissmeyer et al. Journal of Chromatography A, vol. 935, 2001, pp. 93-103.*
Draisci et al. Jounral of Chromatography A, vol. 870, 2000, pp. 511-522.*
Tiller et al. Journal of Chromatography A, vol. 771, 1997, pp. 119-125.*
Kissmeyer et al., Determination of the vitamin D analog EB 1089 (seocalcitol) in human and pig serum using liquid chromatography-tandem mass apectrometry, Journal of Chromatography. Biomedical Applications, Elsevier, Amsterdam, NL. vol. 740. No. 1, Mar. 2000, 117-128.

Jonsson et al., Determination of cortisol in human saliva using liquid chromatography-electrospray tandem mass spectrometry, Journal of Chromatography B: Biomedical Sciences & Applications, Elsevier Science Publishers, NL, vol. 784, No. 1, Jan. 2003, 63-68.
Fredline et al., A reference method for the analysis of aldosterone in blood by high-performance liquid chromatography-atmospheric pressure chemical ionization-tandem mass spectrometry, Analytical Biochemistry, vol. 252, No. 2, 1997, 308-313.
Leinonen et al., Liquid chromatography/mass spectrometry in anabolic steroid analysis: optimazation and comparison of three ionization techniques: electrospray ionization, atmospheric pressure chemical ionization and atmospheric presssure photoionization, Journal of Mass Spectrometry, vol. 37, No. 7, Jul. 2002, 693-698.
Vogeser et al., Determination of serum cortisol by isotope-dilution liquid-chromatography electrospray ionization tandem mass spectrometry with on-line extraction, Clinical Chemistry and Laboratory Medicine, vol. 39, No. 10, Oct. 2001, 944-947.
Robb et al., Atmospheric pressure photoionization: An ionization method for liquid chromatography—Mass spectrometry, Analytical Chemistry, Aug 2000, United States, vol. 72, No. 15, 3653-3659.
Analyze additional compound classes with the PhotoSpray™ atmospheric pressure photoionization source, Product Bulletin, Applied Biosystems, MDS Sciex, Online! 2002.
Choi et al., Rapid HPLC-Electrospray Tandem Mass Spectrometric Assay for Urinary Testosterone and Dihydrotestosterone Glucuronides from Patients with Benign Prostate Hyperplasia, Clinical Chemistry, vol. 49, No. 2, 2003, 322-325.
Biancotto et al., Determination of 17 β-estradiol in bovine plasma: development of a highly sensitive technique by ion trap gas chromatography-tandem mass spectrometry using negative chemical ionization+, Journal of Mass Spectrometry, 2002, vol. 37, 1266-1271.
Lai, et al., Rapid Screening Assay of Congenital Adrenal Hyperplasia by Measuring 17 α-Hydroxyprogesterone with High-Performance Liquid Chromatography/Electrospray Ionization Tandem Mass Spectrometry from Dried Blood Spots, Journal of Clinical Laboratory Analysis, vol. 16, 2002, 20-25.
Vierhapper et al., Reduced Production Rates of Testosterone and Dihydrotestosterone in Healthy Men Treated with Rosiglitazone, Metabolism, vol. 52, No. 2, Feb. 2003, 230-232.
Alary et al., Comparative Study: LC-MS/MS Analysis of Four Steroid Compounds Using a New Photoionization Source and a Conventional APCI Source, Proceedings of the 49th ASMS Conference on Mass Spectrometry and Allied Topics, Chicago, Illinois, May 27-31, 2001.

\* cited by examiner

*Primary Examiner*—Maureen M Wallenhorst
(74) *Attorney, Agent, or Firm*—Torys LLP

(57) ABSTRACT

Methods, systems and kits for the simultaneous or sequential analysis of a multitude of steroid hormones by mass spectrometry are disclosed. The methods require minimal sample size and minimal preparation time. The methods include ionizing the hormones and analyzing the hormones by mass spectrometry. In addition, methods, systems and kits for the simultaneous or sequential analysis of steroid hormones are disclosed including ionization of the steroid hormones by photoionization.

33 Claims, 6 Drawing Sheets

STEROID HORMONE ANALYSIS BY MASS SPECTROMETRY

FIELD OF THE INVENTION

The present invention combines the fields of hormone analysis and mass spectrometry. In particular the invention relates to analyzing steroid hormones using mass spectrometry.

BACKGROUND OF THE INVENTION

Hormones are biological messengers. They are synthesized by specific tissues (glands) and are secreted into the blood. The blood carries them to target cells where they act to alter the activities of the target cells.

Hormones are chemically diverse, and are generally categorized into three main groups: (1) small molecules derived from amino acids, for example thyroxine, (2) polypeptides or proteins, for example insulin and thyroid-stimulating hormone, and (3) molecules derived from cholesterol, for example steroids.

An important class of hormone is the thyroid hormones. Examples of thyroid hormones are thyroxine (T4) and tri-iodothyronine (T3). Both T4 and T3 enter cells and bind to intracellular receptors where they increase the metabolic capabilities of the cell by increasing mitochondria and mitochondrial enzymes.

Steroids make up another important class of hormones. Examples of steroid hormones include estrogens, progesterone and testosterone. Estrogen is the name of a group of hormones of which there are three principle forms, estrone, estradiol and estriol. Estrogens and progesterone cause the development of the female secondary sexual characteristics and develop and maintain the reproductive function. Testosterone develops and maintains the male secondary sex characteristics, promotes growth and formation of sperm. Steroids enter target cells and bind to intracellular receptors and then cause the production of mRNA coding for proteins that manifest the changes induced by steroids.

The accurate analysis and quantification of hormones is becoming more important. For example, estrogen and estrogen like compounds are playing an ever-increasing role in today's society through hormone replacement therapy. Also, the analysis and quantification of estrogen and estrogenike compounds helps in the management of estrogen-related diseases, like breast cancer.

Presently, the common methods of hormone analysis use immunoassay techniques. Table 1 lists the common hormones and the current methods for their analysis.

For example, estriol is analyzed by a radioimmunoassay utilizing radiolabelled antigen (iodine 125) in competition with unlabelled estriol in the sample, for a known amount of antibody. The assay is read using a gamma counter.

Androstenedione is analyzed using an enzyme immunoassay comprising horseradish peroxidase. Unlabeled antigen in the sample is in competition with enzyme labeled antigen for a fixed number of antibody binding sites. The assay is read using a microtitre plate enzyme immunoassay reader.

Several hormones are currently analyzed using a chemiluminescent immunoassay. For example, progesterone, testosterone, cortisol and T3 are analyzed using this method. The assay utilizes an assay-specific antibody-coated bead. The assay is read using a photon counter.

However, the current immunoassays are disadvantageous for the following reasons:

(1) Immunoassays are specific to one hormone, therefore every hormone must be analyzed separately.
(2) Numerous kits must be purchased and procedures must be learned for each hormone being analyzed.
(3) Various instruments to read the results from the immunoassays must be purchased. For example, the analysis of estriol and progesterone from a sample requires both a gamma counter and a photon counter.
(4) The kits for the assays can be expensive.
(5) The current immunoassays lack specificity and may show approximately 15 fold difference in results using kits from different manufacturers [1]. Table 2 provides the mean low and high values for a number of steroids using different immunoassays currently available, illustrating their lack of specificity.
(6) The procedures involve many steps and can take a significant amount of time.
(7) In the case of a radioimmunoassay, precautions are necessary because of the radioisotopes involved.

More recently, hormones have been analysed and quantified by mass spectrometry. However, there are several disadvantages to these methods.

For example, a method of analyzing urinary testosterone and dihydrotestosterone glucuronides using electrospray tandem mass spectrometry has been described [2]. The method involves a complex system employing high performance liquid chromatography (HPLC) and a three-column two-switching valve. The shortcomings include the following: (i) the hormone glucuronides were analyzed, not the hormones, (ii) the method is applicable to urine only and (iii) only two analytes were analysed simultaneously, (iv) the limit of detection (LOD) was 200 pg ml$^{-1}$ for testosterone and the limit of quantification was 10 ug L$^{-1}$ for dihydrotestosterone and (v) the method is complex.

Another publication discloses a method for the determination of estradiol in bovine plasma by an ion trap gas chromatography-tandem mass spectrometry technique [3]. The shortcomings include the following: (i) only one analyte was analyzed, (ii) 4 ml of plasma was required for the analysis of one analyte, (iii) the limit of detection was 5 pg ml$^{-1}$, and (iv) derivation was required because the method employs gas chromatography. Unfortunately, the analysis of estrogens by mass spectrometry is problematic, because they show low sensitivity under conventional electrospray ionization (ESI) or atmospheric pressure chemical ionization (APCI) techniques. Steroid compounds generally lack chemical groups with high proton affinity, so the protonation reaction that normally leads to the formation of the analytical ion is difficult to produce with the standard ESI and APCI sources.

A method for analysis of 17-hydroxyprogesterone by HPLC electrospray ionization tandem mass spectrometry from dried blood spots has also been described [4]. However, this method analyses only one analyte at a time, and requires liquid-liquid extraction, which is laborious and time consuming, with sample extraction alone taking 50 minutes to complete.

Finally, a gas chromatography mass spectrometry method to analyze the production rates of testosterone and dihydrosterone has been disclosed [5].

TABLE 1

Methods and instruments for steroid and thyroid hormones [1]

| ANALYTE | Percentage of Use | Instrument | METHOD |
|---|---|---|---|
| Androstenedione | 35% | DSL solid | EIA |
| 11-Deoxycortisol | 50% | ICN Immuchem DA | RIA |
| DHEA Sulfate | 39% | DPC Immulite | ECIA |
| Estradiol | 16% | Bayer ADVIA Centaur | FIA |
| Estriol, unconjugated | 25% | DSL liquid | RIA |
| Estriol, Total | 50% | DPC Coat-a-Count | RIA |
| 17-Hydroxyprogesterone | 51% | DPC Coat-a-Count | RIA |
| Progesterone | 23% | Bayer ADVIA Centaur | CIA |
| Testosterone | 29% | Bayer ADVIA Centaur | CIA |
| Testosterone, Free | 65% | DPC Coat-a-Count | RIA |
| Aldosterone | 76% | DPC Coat-a-Count | RIA |
| Cortisol | 25% | Bayer ADVIA Centaur | CIA |
| T3 | 29% | Abbott Axsym | FPIA |
| T3, Free | 31% | Bayer ADVIA Centaur | CIA |
| T4 | 30% | Abbott Axsym | FPIA |
| T4, Free | 34% | Abbott Axsym | FPIA |

RIA: Radioimmunoassay
EIA: Enzyme Linked Immunoassay
FPIA: Fluorescence Polarization Immunoassay

SUMMARY OF THE INVENTION

The invention provides a fast and accurate method of hormone analysis and quantification using a mass spectrometer.

A plurality of hormones can be analyzed simultaneously or sequentially. The procedure allows for as little as 700 µL of a sample containing steroid hormone to be analyzed. In addition, minimal sample preparation time is required.

The invention permits the analysis of hormones in a number of complex matrices as they might be found in nature, e.g. the human body. For, example, hormone analysis can be performed on samples of blood, saliva, serum, plasma and urine.

There are several advantages to this invention:
(1) It provides a total and specific analysis for hormones in a sample. The present method allows for the analysis of many hormones simultaneously or sequentially.
(2) The procedure does not require an immunoprecipitation reaction. The majority of other methods for hormone analysis required an immunoassay. Immunoassays are expensive, specific to a particular analyte and involve several steps.
(3) The present invention requires minimal sample preparation time. For example, preparing a sample for hormone analysis can be done within 6 minutes.
(4) The procedure does not require a large sample size. A plasma or serum sample can be as small as 700 µL for steroid hormones. The current methods for hormone analysis that utilize mass spectrometry require 4-15 mL of plasma.
(5) The invention uses simple preparation techniques that are easy to use and highly reproducible.
(6) The invention permits analysis to be performed on a variety of sample types.
(7) The invention permits the analysis of hormones in a sample of saliva or urine which permits simple sample acquisition and the remote submission of samples to a clinic for analysis. In previous other clinical methods, samples are taken by invasive means directly from the patient in a clinic.
(8) The analysis by mass spectrometry is highly accurate. In addition, the procedure of the present invention is highly reproducible.
(9) The invention is highly sensitive for estrogens, unlike other methods. Depending on the nature of the estrogen, sensitivity is increased by a factor of 2 to 100, when compared with other methods.
(10) No prior derivation reaction is required to analyze estrogens by this method.
(11) The invention permits the analysis of a wide range of hormone concentrations. For example, the limit of detection can be as low as 5 pg ml$^{-1}$ for testosterone with standard solutions.

Accordingly, there is provided a use for a mass spectrometer in simultaneously or sequentially analyzing a sample for a plurality of hormones in a fast, simple and accurate way. The sample may be, for example, serum, plasma, urine or saliva.

There is also provided a system for the fast, simple and accurate analysis of a plurality of hormones comprising: reagents for the preparation of the sample, reagents for analysis by a mass spectrometer, and the mass spectrometer to perform the analysis.

There is also provided a kit, comprising the various reagents required for simultaneously or sequentially analyzing, within a sample, a plurality of hormones, including steroid hormones, thyroid hormones and other hormones. The kit may include a standard solution of the hormones of interest, compounds as internal standards, mobile phase solutions, methods and tools for the separation of hormones from the sample, for example an HPLC column, and quality control specimens.

Accordingly, there is provided a method for the simultaneous or sequential analysis of one or more hormones comprising ionizing the hormones and analyzing the hormones by mass spectrometry.

Accordingly, there is also provided a method for simultaneous or sequential analysis of one or more hormones comprising: obtaining a sample containing or suspected of containing one or more hormones, removing proteins from the sample, extracting the hormones from the sample, ionizing the hormones, and analyzing the hormones in a mass spectrometer.

Accordingly, there is also provided a method for the simultaneous or sequential analysis of one or more steroid hormones comprising: obtaining a sample containing or suspected of containing one or more steroid hormones, removing proteins from the sample, extracting the steroid hormones from the sample, ionizing the steroid hormones by photoionization, in the negative or positive mode, and analyzing the hormones in a mass spectrometer.

Accordingly, there is also provided a method for the analysis of one or more steroid hormones comprising: obtaining a sample containing or suspected of containing one or more steroid hormones, removing proteins from the sample, extracting the steroid hormone from the sample, ionizing the steroid hormone by photoionization, in the negative or positive mode, and analyzing the hormone in a mass spectrometer.

Accordingly, there is also provided a method for simultaneous or sequential analysis of a plurality of thyroid hormones and a plurality of steroid hormones comprising: obtaining a sample containing or suspected of containing a plurality of hormones, removing proteins from the sample, extracting the hormones from the sample, ionizing the steroid hormones in the negative or positive mode by photoionization, ionizing the thyroid hormones, for example by electrospray ionization, and analyzing the hormones in a mass spectrometer.

BRIEF DESCRIPTION OF THE DRAWINGS

The invention, including the best approaches known to the inventors, can be better understood with reference to the following detailed description taken in combination with the following drawings, in which.

DETAILED DESCRIPTION OF THE EXEMPLIFIED EMBODIMENT

Figure 1:
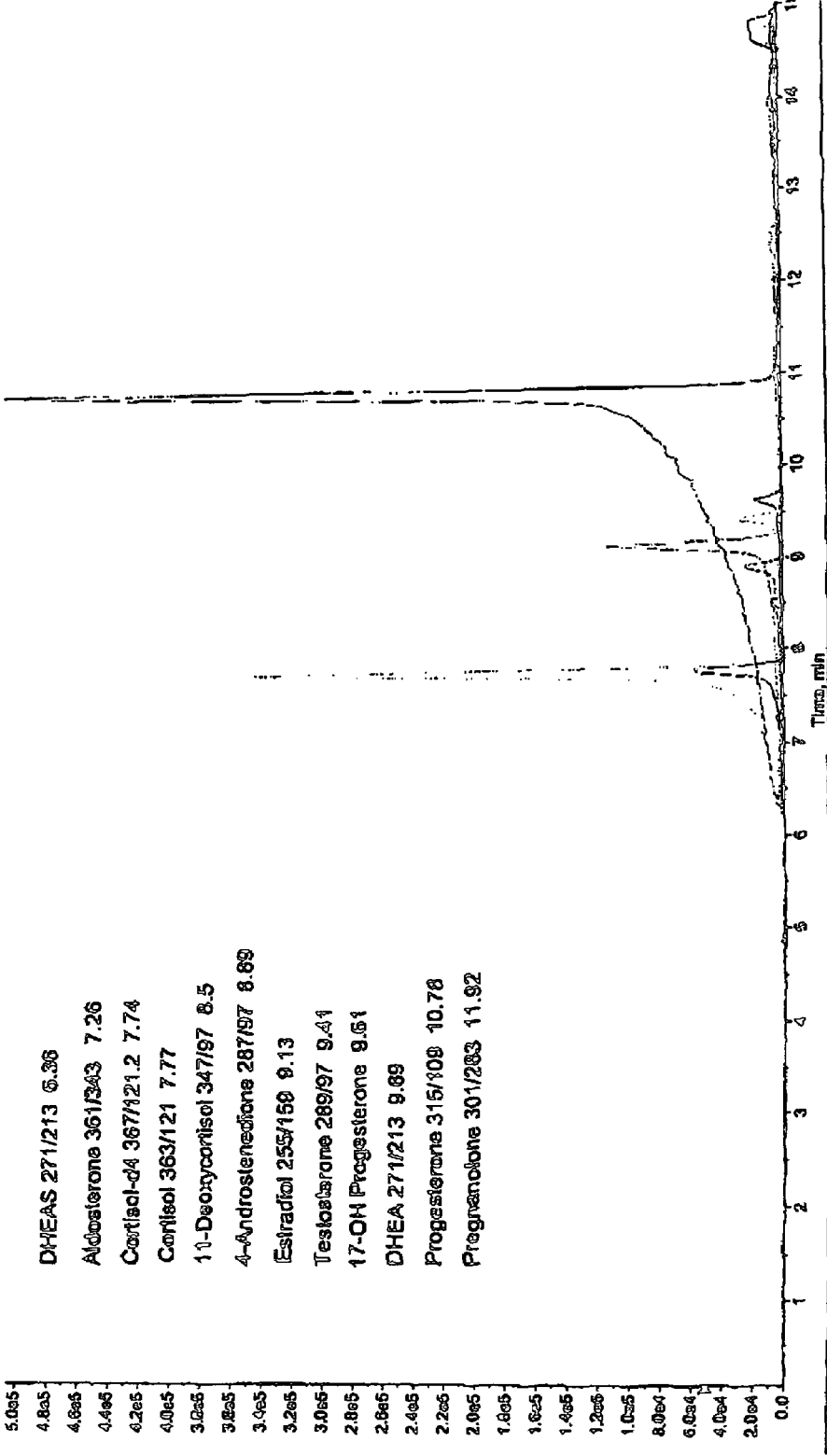
FIG. 1 is a mass spectrum of a sample containing steroids. The steroids in the sample are listed, including their mass profiles and their respective retention times. The sample was analyzed in the positive mode.

The invention provides methods of analysis for hormones. The hormones may include:
Dehydroepiandrosterone (DHEA)
Dehydroepiandrosterone sulphate (DHEAS)
Aldosterone
Cortisol
11-Deoxycortisol
Androstenedione
Testosterone
Estradiol
17-OH Progesterone
Progesterone
Allopregnanolone
16-OH Estrone
2-OH Estrone
Estrone
Estriol
Vitamin D
thyroxine
triiodothyronine
catecholamines
metanephrines
other steroid hormones
other thyroid hormones
other small peptide hormones
other amines Sample Any sample containing or suspected of containing a hormone can be used, including a sample of blood, plasma, serum, urine or saliva. The sample may contain both free and conjugated or bound hormones. A sample size of at least about 700 μL for steroid hormones is presently preferred.

Deproteinization

The sample is de-proteinated. This can be done by conventional techniques known to those skilled in the art. For example, a sample can be de-proteinated with acetonitrile, containing internal standard, followed by vortexing and centrifugation. The internal standard may be, for example, the deuterated hormone.

Separation of Hormones from the Sample

The hormones are separated by methods known to those skilled in the art. For example, the hormones may be separated by liquid chromatography through a column. The column may be a C-18 column. The hormones are subsequently eluted from the column.

Introduction of Hormones into a Mass Spectrometer

The hormones are then introduced into a mass spectrometer. Optionally, the separation step and step of introducing the hormones into a mass spectrometer can be combined using a combined liquid chromatography spectrometry apparatus (LC/MS). This procedure is based on an online extraction of the injected sample with subsequent introduction into the mass spectrometer using a built-in switching valve. LC/MS and liquid chromatography-tandem mass spectrometry (LC-MS-MS) are specific and offer simple approaches to sample preparation without sample derivation steps, and are presently preferred for use in the present invention.

Isotope Dilution Tandem Mass Spectrometry

Isotope dilution tandem mass spectrometry incorporates additional dilution steps that act as an internal calibration so that an independent isotopic reference material is not required. It avoids the need to measure the isotope ratio of the highly enriched spike directly, and enables the final results to be arranged as a combination of measurements that are largely insensitive to instrumental bias and drift. Consequently, it has the potential to extend the scope of application of isotope dilution tandem mass spectrometry to include analysis for which reference materials with certified isotope ratios are not available or where contamination of the instrument by the highlyenriched spike causes difficulty.

Instrumentation and Ionization Techniques

The hormones are subjected to ionization. Various ionization techniques can be used. For example, photoionization, electrospray ionization (ESI), atmospheric pressure chemical ionization (APCI), and electron capture ionization may be used. Preferably, photoionization is used when analyzing steroid hormones. It is presently preferred that an atmospheric pressure photoionization (APPI) source be used when analyzing steroid hormones.

The following mass spectrometers can be used: any tandem-mass spectrometer, including hybrid quadrupole-linear ion trap mass spectrometers and liquid chromatography-tandem mass spectrometers such as the API 2000™ mass spectrometer, the API 3000™ mass spectrometer, and the API 4000™ mass spectrometer, described in U.S. Pat. Nos. 4,121,099; 4,137,750; 4,328,420; 4,963,736; 5,179,278; 5,248,875; 5,412,208; and 5,847,386 (Applied Biosystems/MDS SCIEX, Foster City, Calif./Concord Ontario, Canada). When analyzing steroid hormones, a spectrometer with a photospray ion source, such as the API 3000™ mass spectrometer, is presently preferred.

Ionization may be performed by utilizing the mass spectrometer in the negative or the positive mode. Factors such as a particular analyte's tendency to give rise to a particular ion form, as is known to those skilled in the art, may make either the negative mode or the positive mode more preferable. For example, analysis in the positive mode is typically made for DHEA, Aldosterone, Cortisol, 11-Deoxycortisol, Androstenedione, Testosterone, Estradiol, 17-OH Progesterone, Progesterone, Allopregnalone, and Vitamin D whereas analysis in the negative mode is typically made for 16-OH Estrone, 2-OH Estrone. Estriol and DHEAS. However, it is possible to analyze any of the hormones in either positive or negative mode.

Hormones are identified on the basis of the mass to charge ratio of their molecular ions and fragment ions, as is known to those skilled in the art. When the hormones are purified by liquid chromatography, they can also be identified by their retention times.

Hormones are quantified by their intensity as determined in the mass spectrometer in counts per second. Calibration curves for known concentrations of the hormones are established for comparison.

EXAMPLES

The invention will now be demonstrated using the following examples, provided to demonstrate but not limit the embodiments of the present invention:

1. Analysis of a Sample for Steroid Hormones

A sample of 800 μL of plasma was used. Proteins were precipitated with 1.2 mL of acetonitrile, containing deuterated internal standard, and vortexed. The sample was centrifuged, and 1.7 mL of the supernatant was injected onto a C-18 column coupled to a LC/MS/MS. The column was washed with 2% methanol in 5 mM ammonium acetate for 3 minutes. The valve on the column was switched and the sample was eluted in a methanol gradient of 2 to 100%. The total run time was 12 minutes. Slight adjustments to the volumes, concentrations and times described can be made, as is known to those skilled in the art.

1.7 ml of the eluant was introduced into the mass spectrometer and the sample was ionized by photoionization and analyzed in an API-3000™ mass spectrometer, in the negative or positive mode as described above.

Figure 2:
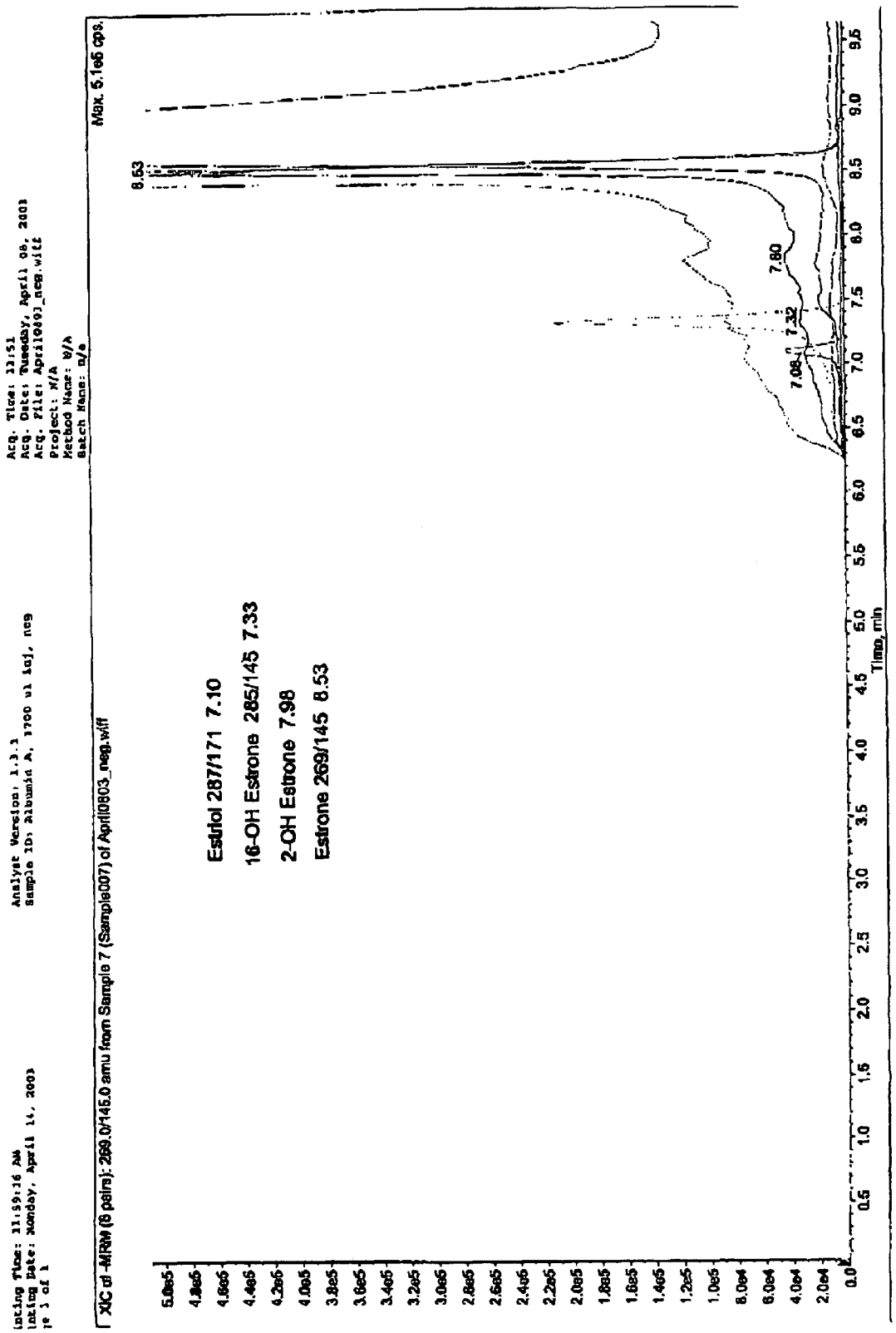
FIG. 2 is a mass spectrum of a sample containing steroids. The steroids in the sample are listed, including their mass profiles and their respective retention times. The sample was analyzed in the negative mode.
Figure 3:
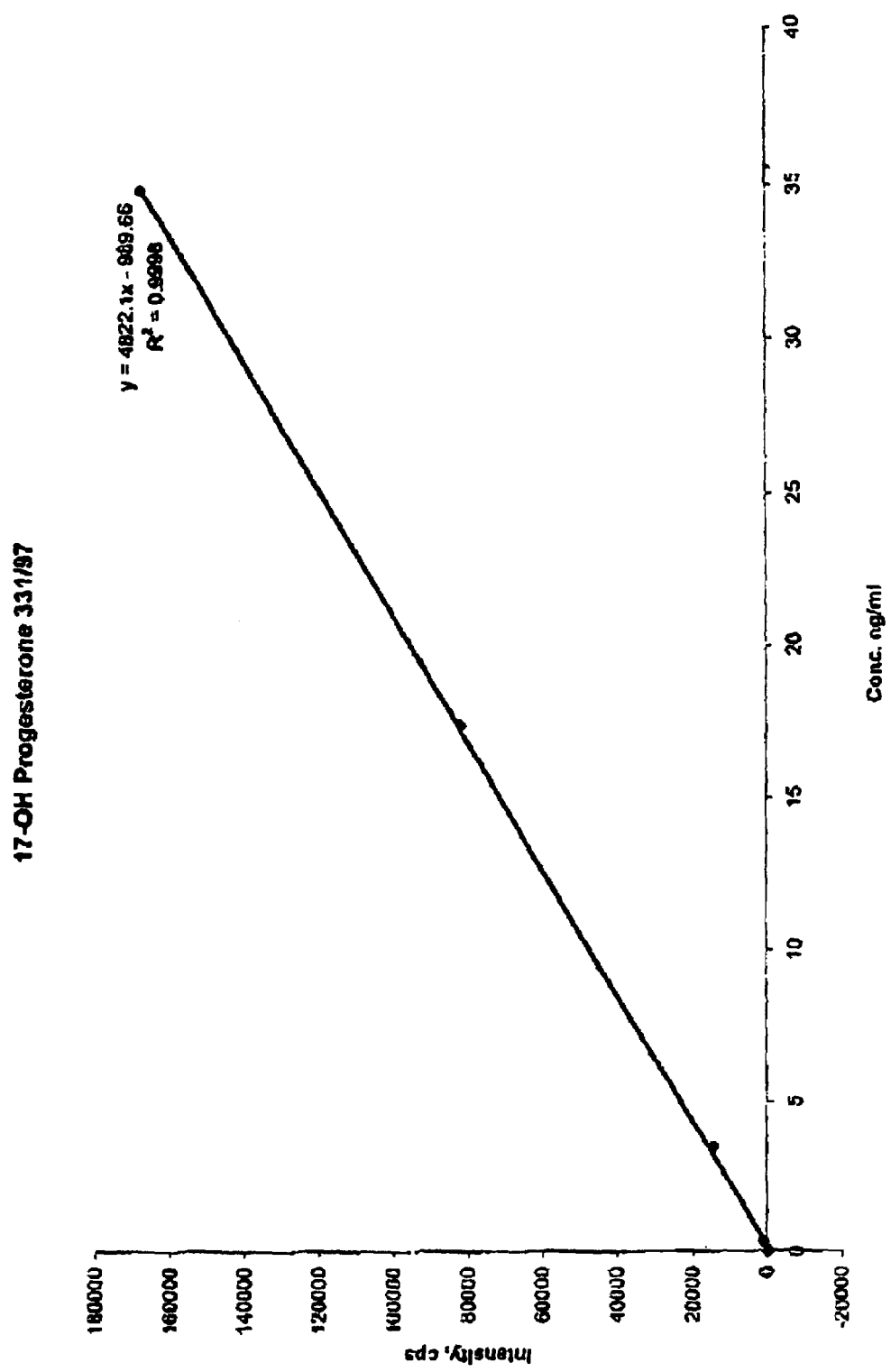
FIG. 3 is a calibration curve for 17-OH Progesterone.
Figure 4:
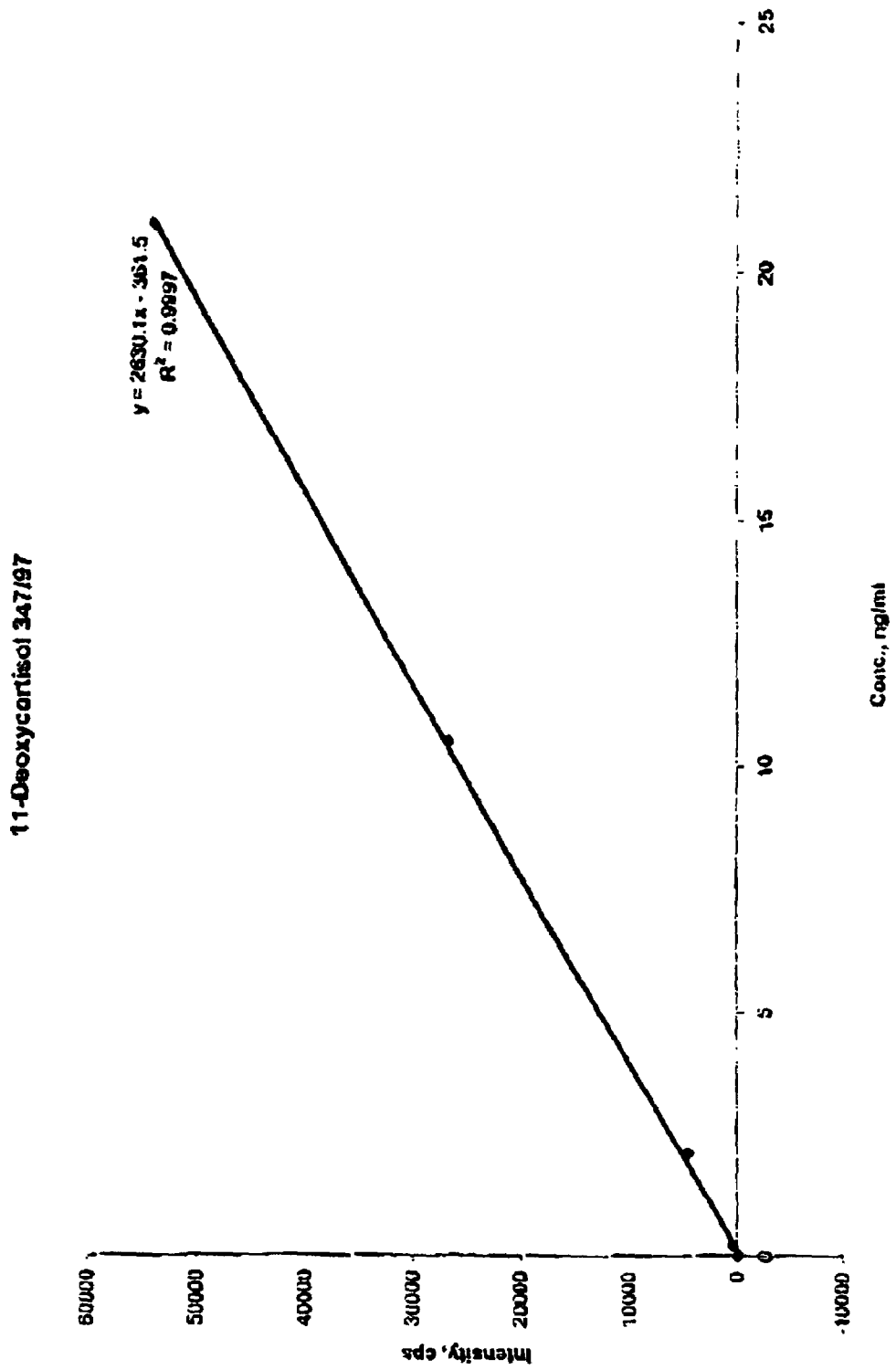
FIG. 4 is a calibration curve for 11-Deoxycortisol.
Figure 5:
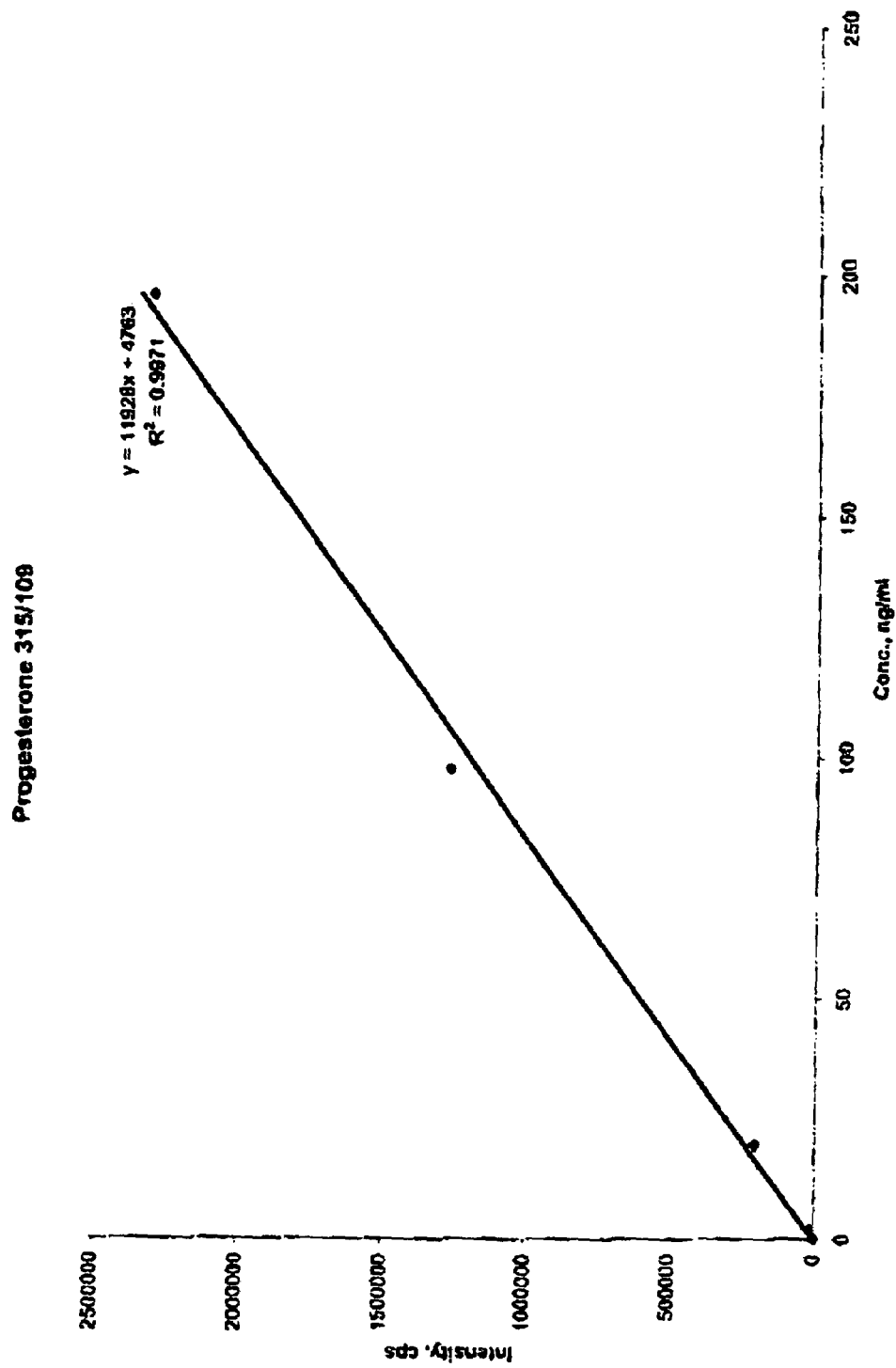
FIG. 5 is a calibration curve for Progesterone.

FIGS. 1 and 2 show the analysis of steroid hormones in the positive and negative modes. FIGS. 3, 4 and 5 show calibration curves for 17-OH Progesterone, 11-Deoxycortisol and Progesterone respectively.

This demonstrates a simple method of preparing a complex biological matrix for analysis of steroid hormone content, and a sensitive analytical method that permits the simultaneous analysis of multiple hormones.

2. Analysis of a Sample for Steroid Hormones

Described below is an example demonstrating a method that permits the simultaneous measurement of 9 steroids in a 760 μL of serum or plasma sample, without derivatization and with minimal sample workup-acetonitrile protein precipitation. The reliability of the method has been evaluated by correlation with currently used immunoassays, and assessment of within-day and between-day imprecision, recovery and accuracy. Comparison of results obtained by tandem-mass spectrometry (tandem MS) with the All Method Mean (CAP PT Program, 2002) has also been made [6].

Materials and Methods

Chemicals: Androstenedione [4-Androstene-3,17-dione], testosterone [4-Androsten-17β-ol-3-one], dehydroepiandrosterone (DHEA, [5-Androsten-3β-ol-17-one]), sodium dehydroepiandrosterone 3-sulfate (DHEAS, [5-Androsten-3β-ol-17-one sulfate, sodium salt], cortisol [4-Pregnen-11β, 17α,21-triol-3,20-dione], 11-deoxycortisol [4-Pregnen-17α, 21-diol-3,20-dione], progesterone [4Pregnen-3,20-dione], 17α-hydroxyprogesterone [4-Pregnen-17β-ol-3,20-dione], 17β-estradiol [1,3,5(10)-Estratriene-3,17,β-diol], Estriol [1,3,5(10)-Estratriene-3,16α,17β-triol], ammonium acetate, and bovine albumin (96%) were purchased from Sigma-Aldrich (St. Louis, Mo.). Deuterium labeled internal standard: testosterone-1,2-$d_2$, cortisol-9,11,12,12-$d_4$, and estradiol-2,4,16,16-$d_4$ were from Cambridge Isotope Laboratory, Inc. (Andover, Mass.); 4-androstene-3,17-dione-2,2,4,6,6,16,6-$d_7$, dehydroepiandrosterone-16,16-$d_2$, 4-pregnen-17α-ol-3, 20-dione-2,2,4,6,6,21,21,21-$d_8$, 11deoxycortisol-21,21-$d_2$, estriol-2,4-$d_2$, and progesterone-2,2,4,6,6,17a,21,21,21-$d_9$ were from C/D/N Isotopes Inc. (Pointe-Claire, Quebec, Canada). HPLC grade water and methanol were obtained from Burdick & Jackson (Muskegon, Mich.). Optima-grade acetonitrile and toluene were from Fisher Scientific (Fair Lawn, N.J.). All chemicals except noted otherwise had a purity of at least 98%, as reported by the manufacturer.

Standard solutions: Stock solutions of 1.0 mg/mL in methanol were prepared for each steroid of interest and stored at −20° C. Working profile standard solutions at various concentrations were prepared as follows: appropriate amounts of the stock solutions were mixed and diluted with methanol to obtain a solution containing 7.81 μg/mL of 11-deoxycotisol, 2.96 μg/mL of 17-hydroxyprogesterone, 1.26 μg/mL of androstenedione, 0.344 μg/mL of estradiol. 2.73 μg/mL of DHEA. 2.09 μg/mL of testosterone, 3.31 μg/mL of progesterone, 68.1 μg/mL of cortisol, and 469.4 μg/mL of DHEAS. This mixed steroid standard solution was added to a 4% solution of albumin in water to provide steroid profile standards that were diluted 10, 20, 100, 200, 500, and 1000 fold. These seven solutions, including the blank albumin solution, were then used to prepare a calibration curve covering the clinically important range of concentration for each steroid. A solution of 80 ng/mL for each of eight deuteriumabeled steroids in acetonitrile was used as internal standard and precipitant of proteins either for the albumin standards or serum/plasma samples. Quality control (QC) samples at three concentration levels were purchased from BioRad (Irvine, Calif.) and were used to evaluate the within-day and between-day precision as well as the accuracy of the method.

Sample preparation: 760 μL of each profile standard or serum sample containing steroids of interest was placed into a 2.0 mL conical plastic centrifuge tube. 1140 μL of internal standard solution in acetonitrile was added to the tube to precipitate the proteins in the sample. The tubes were capped, vortexed vigorously for at least 30 s and centrifuged at 13000 g for 10 min. The supernatant in the tubes was transferred into autosampler vials for injection into the LC-MS-MS system. Sample preparation was performed at room temperature.

LC-MS-MS analysis: We used an SCIEX (Applied Biosystems/MDS SCIEX, Foster City. Calif. USA/Concord, Ontario, Canada) API-3000™ triple quadrupole tandem mass spectrometer equipped with an atmospheric pressure photoionization (Applied Biosystems/MDS SCIEX, Foster City, Calif. USA/Concord, Ontario, Canada) source. The Photoionization lamp used was a 10 eV Cathodeon Ltd. type number PKS100 krypton discharge lamp. Nitrogen produced by a high purity nitrogen generator (PEAK Scientific Instruments Ltd., Chicago. Ill.) was employed as curtain, nebulizer, collision, and lamp gases. Unit mass resolution was set in both mass-resolving quadrupole Q1 and Q3. The HPLC system consisted of three Shimadzu SCL-10Avp pumps, Shimadzu SIL-HT$_c$ autosampler, and Shimadzu DUG-14A degasser (Shimadzu Corp., Kyoto, Japan). Data were collected by using a Dell Optiplex GX400 workstation and processed by Analyst 1.3.1 software package (MDS SCIEX, Concord, Ontario, Canada).

Aliquots of 1700 μL were injected by the autosampler onto a Supelco LC-18-DB (3.3 mm×3.0 mm, 3.0 mm ID) chromatographic column equipped with Supelco Discovery C-18 (3.0 mm) guard column with identical packing material (Supelco, St. Louis, Mo., USA) at room temperature. The steroids adhered to the column, which was then washed with solvent C, a mixture of 15 mM ammonium acetate and methanol (98:2, v/v, pH 5.5), at a rate of 1.0 mL/min. After 5.0 min of washing the switching valve (VICI, Valco Instruments Co. Inc., Houston, Tex.) was activated and the column was eluted with a gradient (Table 3) at a rate of 0.5 mL/min and the sample was introduced into the mass spectrometer. The column was flushed for 4 min with 100% solvent B (methanol) before the next injection. The dopant (Optima-grade toluene) was delivered into the source by using a syringe pump (model '22', Harvard Apparatus Inc., Holliston, Mass.) at a flow rate of 50 µL/min. Analytes were then quantified in MRM mode.

Calibration, using internal standardization, was done by linear regression analysis over various concentration ranges for the different steroids of interest. For each standard curve, a minimum of six different concentrations was used. Stable isotope dilution was employed for 8 of the 9 steroids. For DHEAS, we employed testosterone-$d_2$ as the internal standard, because we could not find a sensitive and specific MRM transition for the deuterated DHEAS-$d_2$ in positive ion mode. Peak area ratios between target analytes and their respective internal standards were used for quantification.

Precision was evaluated by assaying BioRad Liquichek Immunoassay Plus Control (LOT 40620) in replicates (n=10 for within-day, n=20 for between-day) at three levels of concentration. Accuracy for cortisol, progesterone, and testosterone was evaluated by assaying BioRad Lyphochek Immunoassay Plus Control (LOT 40130), which provides target mass spectrometric values for these steroids.

Results and Discussion

Figure 6:
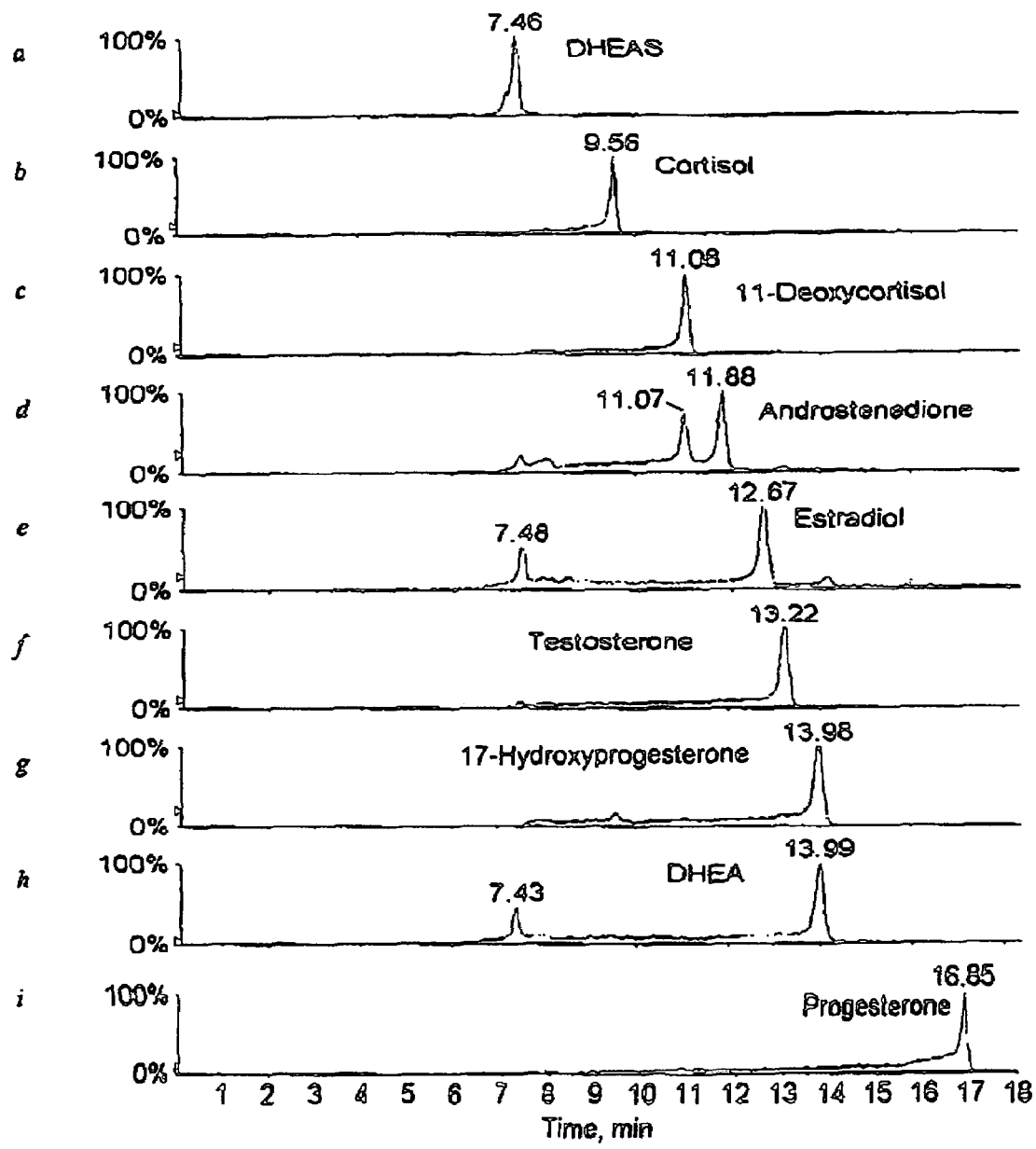
FIG. 6 shows the chromatograms obtained for nine steroids in a standard solution using the assay conditions described in Example 2.

FIG. 6 shows the chromatograms obtained for each of the steroids in a standard solution using the assay conditions described. The nine steroids investigated in positive ion mode and their respective deuterated internal standards were separated well in 18 min. Although both DHEA and 17-hydroxyprogesterone have peaks at 14 min, no interference for each other was observed due to the specificity of the MRM mode in tandem MS. We used the same MRM transition 271→213 for compound DHEA and DHEAS in positive ion mode. Because of the huge difference in concentration in human plasma or in profile standard, the peak of DHEA at 14.1 min is almost invisible in the same panel of DHEAS which has a peak at 7.5 min. Optimal MRM transition, collision energy and declustering potential for each analyte were obtained by continuous infusion of each analyte solution (1.0 µg/mL in water/methanol (50:50, v/v)) separately into the tandem mass spectrometer as recommended by the manufacturer. Table 4 shows the optimum conditions chosen for the steroid profile assay, while Table 5 shows the main working parameters employed. Linear regression analysis (GraphPad Prism version 3.02 for Windows, GraphPad Software, San Diego, Calif.) gave the values shown in Table 6 for correlations of the tandem mass spectrometry method with current immunoassays (IAs). Correlation coefficients obtained were between 0.886 and 0.988. Within-day and between-day imprecision at 3 concentration levels is shown in Table 7. Between-day results gave a coefficient of variation (CV) of 7.1-22% at the low concentration level and of 4.2-13.4% at the high concentration level. Poorest precision was obtained for androstenedione. Accuracy was evaluated using several approaches. Cortisol, progesterone, and testosterone were measured in replicate of 10 on the BioRad Lyphochek Immunoassay Plus Control (LOT 40130) and the mean result obtained. This result compared well with BioRad mass spectrometry values provided (Table 8). Accuracy was also assessed through the addition of known amounts of the steroids to a plasma pool (Table 9) and by method comparison (Table 6). In Table 9, the amount of steroid measured was very close to the target added with the exception of DHEAS, in Table 6, correlation coefficients were excellent. Samples used were either serum or heparinized plasma. The recovery of the nine steroids investigated in positive ion mode was determined at two concentration levels in replicates of five. As shown in Table 9, the mean recoveries of steroids under study were all higher than 82% at both concentration levels except for DHEAS. (for which we could not employ its own deuterated internal standard. It is clear that the recovery of DHEAS is lower than that of the other steroids evaluated.) A comparison between the tandem MS results of the steroids studied and the All Method Mean from CAP PT Program, 2002 is summarized in Table 10. Not surprisingly, tandem MS results were lower than the All Method Mean, ranging from 22.1% for 11-deoxycortisol to 88.7% for DHEAS.

Conclusion

The method described allows for the simultaneous quantitation of 9 steroids in positive ion mode by tandem mass spectrometry within 18 minutes. The method is based on isotope dilution and unlike immunoassays is very specific for the analytes of interest. The method possesses adequate sensitivity (due to use of the APPI source, with the lower level of sensitivity being 100 pg/mL for each steroid) and precision to be used in the routine clinical laboratory. The method has been used for the measurement of steroid concentrations in patient samples. The API4000™ mass spectrometer may be used to measure estradiol below 100 pg/mL. Results have been compared with immunoassay techniques. Generally, tandem mass spectrometry provides lower values no doubt due to improved specificity. The correlation coefficients shown in Table 6 are good. Unlike immunoassays where each steroid has to be assayed separately, the current procedure allows for the simultaneous measurement of many steroids thereby providing a steroid profile on each sample measured. We believe that the improved specificity and simultaneous quantitation features afforded by this method represent distinct advantages over current IAs. No drug interferences have been detected.

In regards to the analysis of Vitamin D, the separation time in chromatography may be lengthened to at least 23 minutes and the gradient may be extended to at least 95% methanol, as compared to other steroid hormones.

Information from this example is contained in Archives of Pathology & Laboratory Medicine, "Steroid Profiles Using Liquid Chromatography-Tandem Mass Spectrometry With Atmospheric Pressure Photoionization Source.", Tiedong Guo MS, Michael Chan PhD and Steven J. Soldin PhD, pages 469-475, April, 2004.

"This work was supported by grant M01-RR13297 from the General Clinical Research Center Program of the National Center for Research Resources, National Institutes of Health, Department of Health and Human Services."

TABLE 2

Problems with Immunoassays Data from CAP PT Program 2002

| Analyte | Low | High |
| --- | --- | --- |
| Androstenedione, ng/dL (nmol/L) | 17.3 (0.604) | 23.1 (0.806) |
| 17-Hydroxyprogesterone, ng/dL (nmol/L) | 16.0 (0.48) | 82.7 (2.48) |
| Estradiol, pg/mL (nmol/L) | 25.7 (94.3) | 220.7 (810.0) |
| Progesterone, ng/mL (nmol/L) | 1.56 (4.96) | 3.85 (12.24) |
| Testosterone, ng/dL (nmol/L) | 20.1 (0.697) | 51.2 (1.777) |

TABLE 2-continued

Problems with Immunoassays Data from CAP PT Program 2002

| Analyte | Low | High |
|---|---|---|
| DHEAS, ug/dL (nmol/L) | 34.9 (9.42) | 59.9 (16.17) |
| Estriol, ng/mL (nmol/L) | 5.57 (19.33) | 20.5 (71.14) |

TABLE 3

Gradient Timetable

| | Time (min) | Solvent A (%) | Solvent B (%) |
|---|---|---|---|
| washing (1.0 mL/min) | 0 | 100 | 0 |
| elution (0.5 mL/min) | 5 | 100 | 0 |
| | 7 | 50 | 50 |
| | 11 | 45 | 55 |
| | 14.5 | 40 | 60 |
| | 17.9 | 20 | 80 |
| | 18 | 100 | 0 |

Solvent A: water/methanol (98:2, v/v).
Solvent B: methanol.
Solvent C, a mixture of 15 mM ammonium acetate and methanol (98:2, v/v, pH 5.5), was used only in positive ion mode.

TABLE 4

MS-MS (MRM) Conditions for the Steroids Analyzed in Positive ion Mode

| Steroid | MRM transition | Collision energy (eV) | Declustering potential (V) | Rt (min) |
|---|---|---|---|---|
| DHEAS | 271→213 | 24 | 21 | 7.5 |
| Estriol* | 287→171 | −50 | −28 | 8.5 |
| Estriol-$d_2$* | 289→147 | −56 | −39 | 8.5 |
| Cortisol | 363→121 | 37 | 23 | 9.6 |
| Cortisol-$d_4$ | 367→121 | 37 | 23 | 9.6 |
| 11-Deoxycortisol | 347→97 | 42 | 22 | 11.1 |
| 11-Deoxycortisol-$d_2$ | 349→97 | 42 | 22 | 11.1 |
| Androstenedione | 287→97 | 31 | 25 | 11.9 |
| Androstenedione-$d_7$ | 294→100 | 31 | 28 | 11.9 |
| Estradiol | 255→159 | 26 | 21 | 12.7 |
| Estradiol-$d_4$ | 259→161 | 25 | 23 | 12.7 |
| Testosterone | 289→97 | 31 | 25 | 13.2 |
| Testosterone-$d_2$ | 291→99 | 37 | 32 | 13.2 |
| 17-Hydroxyprogesterone | 331→97 | 37 | 23 | 14.0 |
| 17-Hydroxyprogesterone-$d_8$ | 339→100 | 39 | 23 | 14.0 |
| DHEA | 271→213 | 24 | 21 | 14.1 |
| DHEA-$d_2$ | 273→213 | 24 | 23 | 14.1 |
| Progesterone | 315→109 | 37 | 24 | 16.9 |
| Progesterone-$d_9$ | 324→100 | 37 | 22 | 16.9 |

*Samples of estriol were run in negative ion mode. Rt indicates retention time.

TABLE 5

Tandem Mass Spectrometer Main Working Parameters

| Parameters | Value |
|---|---|
| Nebulizer gas, psi | 70 |
| Auxiliary gas | 8 |
| Curtain gas | 10 |
| Collision gas | 4 |
| Ion spray voltage*, V | 1400 |
| Probe temperature, °C. | 450 |
| Dwell time per transition, msec | 200 |

*Samples of estriol were run in negative ion mode and ion spray voltage was −1400 V.

TABLE 6

Correlation Between Tandem MS and Immunoassays

| Steroid | $S_{y,x}$ | Equations | n | Correlation coefficient (r) | Concentration Ranges ng/mL (nmol/L) |
|---|---|---|---|---|---|
| DHEAS[a] | 241.5 | y = 1.15x + 43.18 | 50 | 0.971 | 14-3970 (0.378-107.2) |
| Cortisol[b] | 17.98 | y = 1.036x + 18.28 | 50 | 0.983 | 9.71-554 (27-1526) |
| Androstenedione[c] | 0.564 | y = 1.051x + 0.769 | 50 | 0.905 | 0.1-6.8 (0.349-23.73) |
| Estriol[d,*] | 0.271 | y = 1.132x + 0.079 | 13 | 0.959 | 0.8-3.3 (2.78-11.45) |
| Progesterone[e] | 2.176 | y = 1.236x − 0.502 | 50 | 0.988 | 0.215-52.8 (0.684-167.90) |
| DHEA[c] | 1.26 | y = 1.973x + 2.063 | 27 | 0.886 | 0.1-5.5 (0.347-19.09) |
| 11-Deoxycortisol[f] | 0.688 | y = 0.795x + 1.176 | 15 | 0.908 | 0.5-6.0 (1.45-17.4) |
| Testosterone[f] | 0.633 | y = 0.919x − 0.064 | 50 | 0.971 | 0.11-17.2 (0.38-59.68) |
| 17-Hydroxyprogesterone[g] | 0.232 | y = 1.587x + 0.123 | 46 | 0.988 | 0.11-6.07 (0.33-18.21) |
| Estradiol[a] | 1.392 | y = 1.436x + 0.252 | 43 | 0.969 | 0.15-14.1 (0.551-51.75) |

[a]immunoassay/DPC Immulite (Diagnostic Products Corporation);
[b]immunoassay/Bayer ADVIA Centaur;
[c]RIA/Diagnostic Systems Laboratories, RIA indicates radioimmunoassay;
[d]ColorMetric/Bayer;
[e]RIA/DPC Coat-A-Count;
[f]RIA/ICN Pharmaceuticals;
[g]Extracted RIA/Diagnostic Products Corporation.
*Samples of estriol were run in negative ion mode.

TABLE 7

TANDEM MS WITHIN-DAY AND BETWEEN-DAY PRECISION AFTER RUNNING QC

| Steroid | | Level 1 Mean ng/mL (nmol/L) | % CV | Level 2 Mean ng/mL (nmol/L) | % CV | Level 3 Mean ng/mL (nmol/L) | % CV |
|---|---|---|---|---|---|---|---|
| Cortisol | Within-day | 41.36 (114) | 4.6 | 194.9 (547) | 6.2 | 353.9 (975) | 4.9 |
| | Between-day | 39.79 (110) | 7.1 | 192.7 (531) | 6.9 | 341.1 (940) | 6.1 |
| Androstenedione | Within-day | 1.06 (3.69) | 17.5 | 1.85 (6.46) | 9.2 | 4.59 (16.02) | 5.3 |
| | Between-day | 0.9 (3.14) | 22 | 1.82 (6.35) | 18.1 | 4.21 (14.69) | 13.4 |
| Testosterone | Within-day | 0.95 (3.30) | 4.2 | 5.11 (17.74) | 2.8 | 11.0 (3.817) | 2.7 |
| | Between-day | 0.97 (3.37) | 8.7 | 5.06 (17.56) | 8.3 | 11.1 (38.52) | 6.8 |
| 17-OH progesterone | Within-day | 0.83 (2.49) | 7.6 | 3.38 (10.14) | 5.2 | 6.35 (19.05) | 3.7 |
| | Between-day | 0.87 (2.61) | 9.2 | 3.50 (10.5) | 7.1 | 6.70 (20.1) | 6.8 |
| Progesterone | Within-day | 0.57 (1.81) | 7.5 | 5.62 (17.87) | 3.0 | 14.2 (45.16) | 2.5 |
| | Between-day | 0.86 (2.73) | 16.3 | 5.6 (17.81) | 11.4 | 13.6 (43.25) | 8.8 |
| 11-Deoxycortisol | Within-day | 0.80 (2.32) | 8.4 | 7.91 (22.94) | 5 | 78.2 (226.78) | 4.0 |
| | Between-day | 0.78 (2.26) | 12.7 | 7.86 (22.79) | 8.1 | 78.9 (228.81) | 4.2 |
| Estradiol | Within-day | NA | NA | 0.28 (1.03) | 4.3 | 0.60 (2.20) | 3.7 |
| | Between-day | NA | NA | 0.28 (1.03) | 9 | 0.60 (2.20) | 8.5 |
| DHEA | Within-day | NA | NA | 0.84 (2.91) | 7.9 | 2.75 (9.54) | 6.4 |

TABLE 7-continued

TANDEM MS WITHIN-DAY AND BETWEEN-DAY PRECISION AFTER RUNNING QC

| Steroid | | Level 1 Mean ng/mL (nmol/L) | % CV | Level 2 Mean ng/mL (nmol/L) | % CV | Level 3 Mean ng/mL (nmol/L) | % CV |
|---|---|---|---|---|---|---|---|
| | Between-day | NA | NA | 0.87 (3.02) | 9.2 | 2.86 (9.92) | 8.8 |
| DHEAS | Within-day | NA | NA | 404.5 (10.92) | 13.0 | 1372 (37.04) | 9.7 |
| | Between-day | NA | NA | 415 (11.21) | 13.4 | 1436 (38.77) | 12.7 |

Replicate: within-day n = 10, between-day n = 20.
QC: quality control (BioRad Liquichek Immunoassay Plus Control, LOT 40620);
NA: not available due to the lack of sensitivity of the tandem mass spectrometry method at this low level QC.

TABLE 8

Tandem MS Accuracy Running against BioRad QC

| Steroid | | Level 1 Mean ng/mL (nmol/L) | Level 1 Ranges ng/mL (nmol/L) | Level 2 Mean ng/mL (nmol/L) | Level 2 Ranges ng/mL (nmol/L) | Level 3 Mean ng/mL (nmol/L) | Level 3 Ranges ng/mL (nmol/L) |
|---|---|---|---|---|---|---|---|
| Cortisol | BioRad* | 29.6 (82) | 21.9-37.3 (60-103) | 179 (493) | 132-226 (364-623) | 284 (782) | 207-361 (570-994) |
| | Tandem MS | 31.9 (88) | 27.2-34 (75-94) | 186 (512) | 177-197 (488-543) | 287.7 (793) | 264-295 (727-813) |
| Progesterone | BioRad* | 0.88 (2.80) | 0.00-1.76 (0.00-5.60) | 6.96 (22.13) | 4.52-9.4 (14.4-29.9) | 16.5 (52.47) | 10.7-22.3 (34.0-70.9) |
| | Tandem MS | 0.64 (2.04) | 0.54-0.95 (1.72-3.02) | 5.16 (16.41) | 4.62-5.80 (14.7-18.4) | 12.31 (39.14) | 11.7-13.6 (37.2-43.3) |
| Testosterone | BioRad* | 0.94 (3.26) | 0.38-1.51 (1.32-5.24) | 4.78 (16.59) | 3.06-6.5 (10.6-22.6) | 10.2 (35.39) | 6.83-13.6 (23.7-47.2) |
| | Tandem MS | 0.96 (3.33) | 0.89-1.03 (3.09-3.57) | 4.81 (16.69) | 4.44-5.20 (15.4-18.0) | 10.07 (34.94) | 9.66-10.8 (33.5-37.5) |

Replicate: Tandem MS n = 10;
*BioRad: isotope dilution mass spectrometry results of BioRad Lyphochek Immunoassay Plus Control, LOT 40130.

TABLE 9

Recovery from Addition at Two Concentration Levels, ng/mL nmol/L)

| Steroid | Before Addition a | Amount added b | Found c | Difference d c − a | % Recovery e (d/b) × 100 |
|---|---|---|---|---|---|
| Cortisol | 39.38 (109) | 68.1 (188) | 107 (295) | 67.62 (186) | 99.30 |
| | | 681 (1876) | 687.6 (1894) | 648.22 (1786) | 95.20 |
| Androstenedione | 0.08 (0.279) | 1.26 (4.397) | 1.20 (4.188) | 1.12 (3.909) | 88.89 |
| | | 12.6 (43.97) | 11.48 (40.06) | 11.40 (39.79) | 90.48 |
| Estradiol | undetectable | 0.344 (1.262) | 0.321 (1.178) | 0.321 (1.178) | 93.31 |
| | | 3.44 (12.62) | 3.35 (12.29) | 3.35 (12.29) | 97.38 |
| DHEA | 0.61 (2.12) | 2.73 (9.47) | 2.87 (9.96) | 2.26 (7.84) | 82.78 |
| | | 27.3 (94.73) | 24.5 (85.02) | 23.89 (82.90) | 87.51 |
| 11-Deoxycortisol | 0.08 (0.232) | 7.81 (22.65) | 8.09 (23.46) | 8.01 (23.23) | 102.56 |
| | | 78.1 (226.49) | 71.82 (208.3) | 71.74 (208.05) | 91.86 |

TABLE 9-continued

Recovery from Addition at Two Concentration Levels, ng/mL nmol/L)

| Steroid | Before Addition a | Amount added b | Found c | Difference d c − a | % Recovery e (d/b) × 100 |
|---|---|---|---|---|---|
| Testosterone | 0.25 (0.868) | 2.09 (7.25) | 2.14 (7.43) | 1.89 (6.56) | 90.43 |
| | | 20.9 (72.52) | 19.12 (66.35) | 18.87 (65.48) | 90.29 |
| 17-Hydroxyprogesterone | 0.05 (0.15) | 2.96 (8.88) | 2.84 (8.52) | 2.79 (8.37) | 94.26 |
| | | 29.6 (88.8) | 27.46 (82.38) | 27.41 (82.23) | 92.60 |
| DHEAS | 223 (6.02) | 499 (13.47) | 623 (16.82) | 400 (10.80) | 80.16 |
| | | 4990 (134.73) | 3262 (88.07) | 3039 (82.05) | 60.90 |
| Progesterone | 0.067 (0.213) | 3.33 (10.59) | 3.06 (9.73) | 2.99 (9.51) | 89.79 |
| | | 33.3 (105.89) | 31.88 (101.4) | 31.81 (101.16) | 95.53 |

Replicate: n = 5.

TABLE 10

Comparison Between the Results of Tandem MS and the Results from CAP PT Program 2002

| Analytes | Tandem MS/All Method Instruments Mean (%) |
|---|---|
| Androstenedione | 49.9 |
| 17-Hydroxyprogesterone | 79.3 |
| 11-Deoxycortisol | 22.1 |
| Progesterone | 73.7 |
| Testosterone | 85.3 |
| DHEAS | 88.7 |
| Cortisol | 81.4 |
| Estriol | 75.5 |

3. Analysis of Thyroid Hormones and Steroid Hormones

A sample of 100 μL of plasma is used. Proteins are precipitated with 150 μL of acetonirile and vortexed. The sample is centrifuged, and 200 μL of the supernatant is injected onto a C-18 column coupled to a tandem mass spectrometer (LC/MS/MS). The column is washed with 20% methanol in 5 mM ammonium acetate for 3 minutes. The valve on the column is switched and the sample is eluted in a methanol gradient of 20 to 100%. The total run time is 10 minutes. Slight adjustments to the volumes, concentrations and time described can be made, as is known to those skilled in the art.

A sample of the eluant is introduced into an ion-spray ionization chamber and analyzed by API 3000™ mass spectrometer using the negative mode for thyroid hormones in the sample. Steroid hormones in the sample are ionized by photoionization, with the spectrometer in the negative or positive mode as described above.

This demonstrates a simple method of preparing a complex biological matrix for analysis of possible steroid and thyroid hormone content, and a sensitive analytical method that permits the simultaneous analysis of steroid and thyroid hormones.

4. Performance Comparison of Various Ionization Techniques for the Quantification of Estrogens in Biological Fluids Using a Hybrid Quadrupole-Linear Ion Trap Mass Spectrometer A number of different ionization techniques were compared in terms of detection sensitivity for estrogen like compounds. Among these were electron capture of derivatized estrogens, electrospray detection of native and derivatized estrogens, conventional APCI and photoionization. Each source technique was tested by flow injection analysis to determine the ultimate sensitivity.

The resulting preferred ionization technique was photoionization using an ionizable chemical dopant. This photoionization technique is described elsewhere [7], and disclosed in U.S. Pat. No. 6,534,765. It is particularly well adapted to LC/MS/MS analyses as it overcomes the major deficiencies previously observed with direct photoionization of analytes in LC eluents. With this source, large quantities of an ionizable dopant are mixed with the vaporized LC eluent. The vapor mixture is then exposed to an ultra-violet source emitting 10-eV photons. The ultra-violet radiation preferentially ionizes the dopant that in turn initiates a cascade of ion-molecule reactions leading to the formation of the ionized analytical species. Analytical ions are transferred to the orifice of the spectrometer through a transport tube with the assistance of an electrostatic field. Toluene is normally used as ionizable dopant, however, other compounds with the appropriate first ionization energy, proton affinity and physical properties can also be used. Compared to the ionspray and APCI sources, a dopant-assisted photoionization source greatly enhances the ion signal for compounds that lack chemical groups with high affinity for the proton. The atmospheric pressure photoionization (APPI) source has been demonstrated to be significantly more sensitive than APCI for certain compounds. [7] A comparative study employed APPI-tandem mass spectrometry for the detection of steroids in biological matrices, and showed that in both selected ion monitoring (SIM) mode and multiple reaction monitoring (MRM) mode, the signal obtained by photoionization was more intense by a factor of 3 to 10 when compared to the APCI source [8].

The technique was used to identify and characterize low-level concentrations of metabolites using a mass spectrometer with increased multiple reaction monitoring (MRM) precursor ion and neutral loss scan sensitivities. MRM allows for enhanced selectivity through the measurement of parent and daughter ions simultaneously for each of the compounds of interest. Further, Information Dependent Acquisition (IDA) software tools were used to allow the combination of quadrupole scan functionality with the high sensitivity scan functions of the linear ion trap. Enhanced product ion scans were used for qualitative analysis of estradiol and its metabolites present in human saliva.

The results indicate that this technique allows for the identification and characterization of low levels of estradiol and its metabolites in human plasma and saliva.

While the above detailed description describes the exemplifying embodiments of the present invention, it should be understood that the present invention is susceptible to modifications, variations and alterations without deviating from the scope of the invention.

REFERENCES

All references listed herein are incorporated by reference in their entirety.
1. College of American Pathologists Proficiency Survey Report on Y-03, RAP-03 and K-06 specimens for 2003.
2. Choi M H, Kim, J N, Chung B C. Rapid HPLC-Electrospray Tandem Mass Spectrometric Assay for Urinary Testosterone and Dihydrosterone Glucuronides from Patients with Benign Prostate Hyperplasia. Clin Chem 2003; 49(2): 22-325.
3. Biancotto G. Angeletti R. Traldi P, Silvestri M S. Guidugli F. Determination of 17β-Estradiol in Bovine Plasma: Development of a Highly Sensitive Technique by Ion Trap Gas Chromatography-Tandem Mass Spectrometry Using Negative Ion Chemical Ionization. J Mass Spectrom 2002; 37: 1226-1271.
4. Lai C C, Tsai C H, Tsai F J, Wu J Y, Lin W D, Lee C C. Rapid Screening Assay of Congenital Adrenal Hyperplasia by Measuring 7α-Hydroxy-progesterone with High-Performance Liquid Chromatography/Electrospray Ionization Tandem Mass Spectrometry From Dried Blood Spots. J Clin Lab Anal 2002; 16: 20-25.
5. Vierhapper H, Nowotny P. Waldausl W. Reduced Production Rates of Testosterone and Dihydrosterone in Healthy Men Treated with Rosiglitazone. Metabolism 2000; 52(2): 230-232.
6. College of American Pathologists Proficiency Testing Program (CAP PT), Surveys 2002 Y-A Ligands (Special). Data taken from the 2002 survey program and published quarterly throughout 2002 by the College of American Pathologists to participants in the proficiency testing program.
7. Robb D B, Covey T R, Bruins A P. Atmospheric Pressure Photoionization: An Ionization Method for Liquid Chromatography-Mass Spectrometry Anal Chem. 2000; 72:3653-3659.
8. Alary J F. A010942. Comparative Study: LC-MS/MS Analysis of Four Steroid Compounds Using a Now Photoionization Source and a Conventional APCI Source. In Proceedings of the 49th ASMS Conference on Mass Spectrometry and Allied Topics (CD-ROM). Chicago, IL. May 27-31, 2001.

What is claimed is:

1. A method for mass spectrometric analysis of a sample containing a multitude of steroid hormones, comprising the steps:
(a) providing a sample containing a multitude of steroid hormones;
(b) deproteinating the sample;
(c) separating the multitude of steroid hormones from the sample; and
(d) analyzing the multitude of steroid hormones using a mass spectrometer, wherein the multitude of steroid hormones comprises at least four hormones selected from the group consisting of estrogens, testosterones, aldosterone, dehydroepicandrosterone, dehydroepiandrosterone sulphate (DHEAs) and Vitamin D.

2. The method according to claim 1 wherein the at least four steroid hormones are selected from the group consisting of Dehydroepiandrosterone (DHEA), Dehydroepiandrosterone sulphate (DHEAS), Aldosterone, Testosterone, Estradiol, 16-OH Estrone, 2-OH Estrone, Estrone, Estriol and Vitamin D.

3. The method according to claim 1 wherein the sample containing the multitude of steroid hormones is obtained from a biological sample selected from the group consisting of blood, plasma, serum, urine and saliva.

4. The method of claim 3 wherein the biological sample is blood.

5. The method of claim 3 wherein the biological sample is plasma.

6. The method of claim 3 wherein the biological sample is serum.

7. The method of claim 3 wherein the biological sample is urine.

8. The method of claim 3 wherein the biological sample is saliva.

9. The method according to claim 1 wherein size of said sample containing the multitude of steroid hormones is at least about 700 μL.

10. The method according to claim 1 wherein said step of deproteinating the sample comprises:
(a) adding acetonitrile, containing internal standards;
(b) vortexing the sample; and
(c) subjecting the sample to centrifugation.

11. The method according to claim 1 wherein said step of deproteinating the sample comprises subjecting the sample to precipitation with an agent containing internal standards, said agent selected from the group consisting of methanol, ethanol and salt.

12. The method according to claim 1 wherein said step of separating the multitude of steroid hormones from the sample comprises introducing the sample to a liquid chromatography apparatus comprising a column and subsequently eluting the hormones from the column.

13. The method according to claim 12 wherein said step of separating the multitude of steroid hormones from the sample comprises the use of a C-18 column.

14. The method according to claim 1 wherein said step of separating the multitude of steroid hormones from the sample comprises the use of a combined liquid chromatography spectrometry apparatus.

15. The method according to claim 14 wherein the multitude of steroid hormones are introduced into the mass spectrometer directly after being separated from the sample by way of an on-line extraction and use of a built-in switching valve.

16. The method according to claim 1 wherein the mass spectrometer is a liquid chromatography-tandem mass spectrometer.

17. The method according to claim 16 wherein the liquid chromatography tandem-mass spectrometer is equipped with an atmospheric pressure photoionization source.

18. The method according to claim 1 wherein said step of analyzing the multitude of steroid hormones using a mass spectrometer comprises an ionization technique selected from the group consisting of photoioinization, electrospray ionization, atmospheric pressure chemical ionization, and electron capture ionization.

19. The method according to claim 18 wherein said ionization technique is photoionization.

20. The method according to claim 19 wherein said photoionization technique comprises the use of an atmospheric pressure photoionization source.

21. The method according to claim 18 wherein said ionization is performed in positive mode.

22. The method according to claim 18 wherein said ionization is performed in negative mode.

23. The method according to claim 1 wherein said step of analyzing the multitude of steroid hormones using a mass spectrometer comprises multiple reaction monitoring.

24. The method according to claim 1 wherein said step of analyzing the multitude of steroid hormones using a mass spectrometer comprises selected ion monitoring.

25. The method according to claim 1 wherein the multitude of steroid hormones are analyzed simultaneously.

26. The method according to claim 1 wherein the multitude of steroid hormones are analyzed sequentially.

27. A method of instructing an analysis of a sample that contains a multitude of steroid hormones, the method comprising providing instructions to prepare the sample according to steps (b) and (c) of claim 1 and analyze the multitude of steroid hormones from the sample according to step (d) of claim 1, wherein the multitude of steroid hormones comprises at least four hormones selected from the group consisting of estrogens, testosterones, aldosterone, dehydroepicandrosterone, dehydroepiandrosterone sulphate (DHEAs) and Vitamin D.

28. A system for the mass spectrometric analysis of a sample containing a multitude of steroid hormones, comprising:
    (a) reagents for deproteinating the sample, including internal standards;
    (b) reagents for analyzing the multitude of steroid hormones using a mass spectrometer; and
    (c) a mass spectrometer,
    wherein the multitude of steroid hormones comprises at least four hormones selected from the group consisting of estrogens, testosterones, aldosterones, dehydroepicandrosterones, dehydroepiandrosterone sulphates (DHEAs) and Vitamin D.

29. The system according to claim 28 wherein the mass spectrometer is a liquid chromatography-tandem mass spectrometer.

30. A kit for use in mass spectrometric analysis of a sample containing a multitude of steroid hormones, wherein the multitude of steroid hormones comprises at least four hormones selected from the group consisting of estrogens, testosterones, aldosterone, dehydroepicandrosterone, dehydroepiandrosterone sulphate (DHEAs) and Vitamin D, comprising:
    (a) reagents for deproteinating the sample, including internal standards;
    (b) reagents for separating the multitude of steroid hormones from the sample;
    (c) reagents for analyzing the multitude of steroid hormones using a mass spectrometer;
    (d) a solution of four steroid hormones selected from the group consisting of estrogens, testosterones, aldosterone, dehydroepicandrosterone, dehydroepiandrosterone sulphate (DHEAs) and Vitamin D; and
    (e) instructions for analyzing the multitude of steroid hormones using a mass spectrometer.

31. The kit according to claim 30 further comprising:
    (a) mobile phase solutions;
    (b) a chromatography column; and
    (c) a quality control specimen.

32. Use of a mass spectrometer for sequentially or simultaneously analyzing a sample containing a multitude of steroid hormones, comprising:
    (a) providing a sample containing a multitude of steroid hormones;
    (b) deproteinating the sample;
    (c) separating the multitude of steroid hormones from the sample; and
    (d) analyzing the multitude of steroid hormones using a mass spectrometer,
    wherein the multitude of steroid hormones comprises at least four hormones selected from the group consisting of estrogens, testosterones, aldosterone, dehydroepicandrosterone, dehydroepiandrosterone sulphate (DHEAs) and Vitamin D.

33. The use according to claim 32 wherein the mass spectrometer is a liquid chromatography-tandem mass spectrometer.

* * * * *